US010278735B2

(12) United States Patent
Abell et al.

(10) Patent No.: US 10,278,735 B2
(45) Date of Patent: May 7, 2019

(54) PERCUTANEOUS ROD REVISION IMPLANT

(71) Applicant: Warsaw Orthopedic, Inc, Warsaw, IN (US)

(72) Inventors: Jeanine Abell, Memphis, TN (US); Richard Q. Brown, Collierville, TN (US); Larry T. McBride, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 41 days.

(21) Appl. No.: 15/171,905

(22) Filed: Jun. 2, 2016

(65) Prior Publication Data

US 2017/0348024 A1    Dec. 7, 2017

(51) Int. Cl.
*A61B 17/70*    (2006.01)
*A61B 17/56*    (2006.01)

(52) U.S. Cl.
CPC ...... *A61B 17/7011* (2013.01); *A61B 17/7049* (2013.01); *A61B 17/7089* (2013.01); *A61B 2017/564* (2013.01)

(58) Field of Classification Search
CPC .......................... A61B 17/7049; A61B 17/7011
See application file for complete search history.

(56) References Cited

U.S. PATENT DOCUMENTS

| | | | |
|---|---|---|---|
| 5,591,235 A * | 1/1997 | Kuslich | A61B 17/70 606/261 |
| 3,021,399 A1 | 9/2011 | Ritland | |
| 2006/0079892 A1* | 4/2006 | Roychowdhury | A61B 17/7044 606/253 |
| 2008/0177317 A1* | 7/2008 | Jackson | A61B 17/702 606/254 |
| 2008/0177323 A1* | 7/2008 | Null | A61B 17/7041 606/267 |
| 2010/0256683 A1 | 10/2010 | Ilott et al. | |
| 2011/0087287 A1 | 4/2011 | Reeder, Jr. et al. | |
| 2013/0150887 A1 | 6/2013 | McLean et al. | |

* cited by examiner

*Primary Examiner* — Lynnsy M Summitt
*Assistant Examiner* — Tara Rose E Carter

(57) ABSTRACT

A percutaneous revision implant for percutaneously revising an existing implant located in the spine of a patient may include, for example, extending the existing implant construct to span additional portions of the spine of the patient. The percutaneous revision implant comprises a proximal end portion and a distal end portion. The proximal end portion comprises a connector having two opposable walls joined at one end to define a cavity having a first longitudinal axis. The cavity is suitable to receive and engage a rod of the existing implant. The percutaneous revision implant of the invention permits a medical practitioner to extend an existing implant construct without significantly disrupting or removing the existing implant or its component parts. A method of using same is also provided.

20 Claims, 6 Drawing Sheets

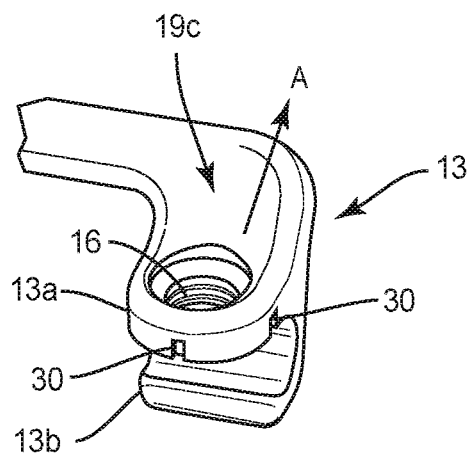
FIG. 3
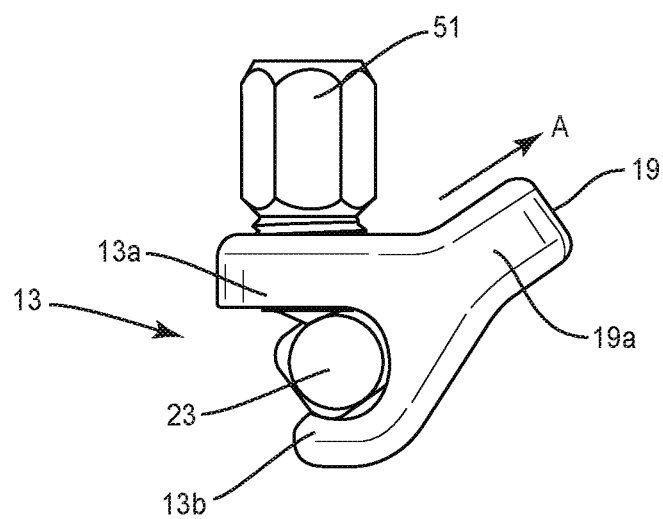
FIG. 4
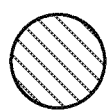     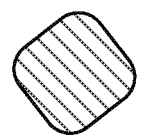
FIG. 5          FIG. 6 ature, life expectancy, or performance of the existing spinal implant, and/or potentially cause deterioration of surrounding bones, discs, vertebrae, hips, knees, etc., or the existing implant. For example, when the abdominal and back muscles strengthen after an implant procedure, the spine may subsequently align or realign, causing the implant or its articulation faces to be impinged as a result of the alignment or realignment. Thus spinal surgeons may need to revise (e.g., extend) an existing spinal implant installed in a patient during a prior surgical procedure. For example, a revision surgery may entail lengthening an existing implant so that it spans additional portions of the spine.

PERCUTANEOUS ROD REVISION IMPLANT

FIELD OF INVENTION

The present invention generally relates to the field of implants, and more particularly, to a percutaneous revision implant for percutaneously revising an existing implant located in the spine of a patient without significantly disrupting or removing components of the existing implant, and methods of using same.

BACKGROUND

Spinal implants are typically implanted when the spine of a patient is dysfunctional (e.g., misaligned, degenerated). Following surgery and/or during or after the healing process, muscular and skeletal alignment or adjustment may occur. Such alignments and adjustments may affect the range of motion of the patient, the effectiveness, life expectancy, or performance of the existing spinal implant, and/or potentially cause deterioration of surrounding bones, discs, vertebrae, hips, knees, etc., or the existing implant. For example, when the abdominal and back muscles strengthen after an implant procedure, the spine may subsequently align or realign, causing the implant or its articulation faces to be impinged as a result of the alignment or realignment. Thus spinal surgeons may need to revise (e.g., extend) an existing spinal implant installed in a patient during a prior surgical procedure. For example, a revision surgery may entail lengthening an existing implant so that it spans additional portions of the spine.

Revision-type surgeries have been developed, but difficulties with typical instrumentation and procedures remain. Ideal installation sites for the revision implant may already be occupied by the existing implant, thereby requiring the medical practitioner to adjust, reposition, remove, or otherwise significantly disrupt the existing implant in order to install the revision implant. Medical practitioners may also need to open up the region of the existing implant to obtain a better view of the surgical site. Such procedures are often performed subcutaneously (i.e., under the skin) and require large incisions, such as in tissue and muscle, and they are thus highly invasive and tend to surgical time, patient trauma, blood loss, tissue damage, post-operative pain, recovery and healing periods, and treatment costs. Current methods to revise existing spinal implants also frequently entail the use of multiple and separate assemblies (e.g., various forms of screws, hook and or connectors linked by rods, wires, or plates), which can be inconvenient, reduce surgical accuracy, and further increase surgery time and costs. It would be desirable to reduce or eliminate these and other drawbacks of revising an existing implant by providing a revision implant having a minimal number of components which may be installed in the spine of a patient using minimally invasive (e.g., percutaneous) procedures, thereby improvement placement accuracy in the spine and reducing or eliminating the need to significantly disrupt or remove the existing implant in order to achieve the desired revision.

The present invention satisfies the above-described needs and provides other benefits and advantages in a novel and nonobvious manner.

SUMMARY

The present invention relates generally to a percutaneous revision implant for percutaneously revising an existing implant located in the spine of a patient. The percutaneous revision implant of the invention permits a medical practitioner to extend an existing implant construct without significantly disrupting or removing the existing implant or its component parts. A method of using same is also provided. While the actual nature of the invention covered herein can only be determined with reference to the claims appended hereto, certain forms of the invention that are characteristic of the preferred embodiments disclosed herein are described briefly as follows.

In one embodiment, a percutaneous revision implant is provided for percutaneously revising an existing implant located in the spine of a patient. The revision achieved may include, for example, extending the existing implant construct to span additional portions of the spine of the patient. The percutaneous revision implant comprises a proximal end portion and a distal end portion. The proximal end portion comprises a connector having two opposable walls joined at one end to define a cavity having a first longitudinal axis. The cavity is suitable to receive and engage a rod of the existing implant. At least one of the connector walls comprises a threaded opening which may be engaged by a securing means, for example, a set screw. The connector may be formed of rigid material. Typically, the connector comprises grooves, notches, ribs or other features for engaging and/or locking onto an instrument for percutaneously delivering the percutaneous revision implant to a desired surgical site in the spinal region of a patient, including but not limited to the delivery instrument disclosed in pending U.S. patent application Ser. No. 15/171,826, herein incorporated by reference.

The distal end portion of the revision implant comprises a percutaneous rod. Typically, the percutaneous rod generally extends along a second longitudinal axis which may be aligned or substantially aligned with the first longitudinal axis of the connector. The percutaneous rod may comprise configurations having various cross-sectional shapes. In one embodiment, the percutaneous rod comprises a cylindrical shape having a circular cross-section. However, some or portion of the percutaneous rod may comprise one or more flat or beveled sides such that a cross-section of the rod may be square, rectangular, or polygonal. The distal end of the percutaneous rod may comprise a tapered tip or other shape suitable to facilitate percutaneous access into tissue and to the surgical site.

The revision implant further comprises an arm which permits a medical practitioner to position the revision implant in a manner that avoids significant disruption or removal of the existing implant. The arm includes proximal and distal ends. A first transition region joins the proximal end of the arm to the connector and a second transition region joins the distal end of the arm to the percutaneous rod. A linear portion having a third longitudinal axis offset from the first and second longitudinal axes is provided between the first and second transition regions. One or both of the transition regions may be sloped or angled. In one embodiment, the arm comprises a C-shape. The arm may comprise any configuration suitable to provide clearance around one or more components of the existing implant, including those comprising a circular, square, rectangular, or polygonal cross-section.

A spinal implant system for percutaneously revising an existing implant is also provided. The spinal implant system generally comprises the aforementioned revision implant, an existing implant, and a new bone fastener. The existing implant is understood to have been installed in the spine of a patient in a prior surgical procedure and comprises at least one existing bone fastener, such as a bone screw comprising a shank having a receiver attached thereto, and at least one existing rod engaged by a portion of the bone fastener (e.g., a receiver). The spinal implant system further comprises a new bone fastener for anchoring in a portion of the spine adjacent the spinal region having the existing implant installed therein. Once installed, the spinal implant system generally comprises the connector of the revision implant engaging a portion of at least one existing rod and the new bone fastener engaging the percutaneous rod of the revision implant. In one embodiment, a means of securing one or more of such engagements is provided, such as a set screw. The second longitudinal axis of the percutaneous rod may be substantially aligned or aligned with a longitudinal axis of the existing rod in the system.

A method of employing a revision implant to revise an existing spinal implant construct, without removing or significantly disrupting the existing implant and/or its hardware components, is also provided in accordance with the invention. The method comprises the steps of obtaining access to a post-operative spinal region of the patient in a minimally invasive manner, such as by providing one or more percutaneous access sites (e.g., stabs, punctures, micro-incisions) in the spinal region of a patient, installing a new bone fastener in a portion of the spine adjacent the spinal region having the existing implant implanted therein through the one or more percutaneous access sites, delivering the revision implant to the surgical site through the one or more percutaneous access sites, engaging the connector arm of the revision implant with the existing rod, and engaging a portion of the percutaneous rod in the new bone fastener. The method may further comprise the step of securing the engagement between the connector and existing rod, between the percutaneous rod and the new bone fastener, or both, with a set screw or other securing component (e.g., wires, hooks). In some embodiments, the method is performed entirely through one percutaneous access site to the spinal region of the patient. The method may further employ an instrument for percutaneously delivering the percutaneous revision implant to a surgical site in the spinal region of a patient, for example the percutaneous delivery instrument disclosed in pending U.S. patent application Ser. No. 15/171,826, by engaging or locking notches, grooves, ribs or other features of the delivery instrument with the aforementioned notches, grooves, ribs or other features of the connector.

It is one object of the present invention to provide improved instruments and methods for percutaneously revising an existing implant installed in the spinal region of a patient with a percutaneous revision implant. Further objects, features, advantages, benefits, and aspects of the present invention will become apparent from the drawings and description contained herein.

BRIEF DESCRIPTION OF THE DRAWINGS

FIG. 3 is an enlarged perspective view of an embodiment of the connector.

FIG. 4 is a side view of an embodiment of the connector engaging at least one existing rod.

FIG. 5 is a cross-section of a cylindrical embodiment of the percutaneous rod.

FIG. 6 is a cross-section of a polygonal embodiment of the percutaneous revision implant.

DETAILED DESCRIPTION

Figure 1:
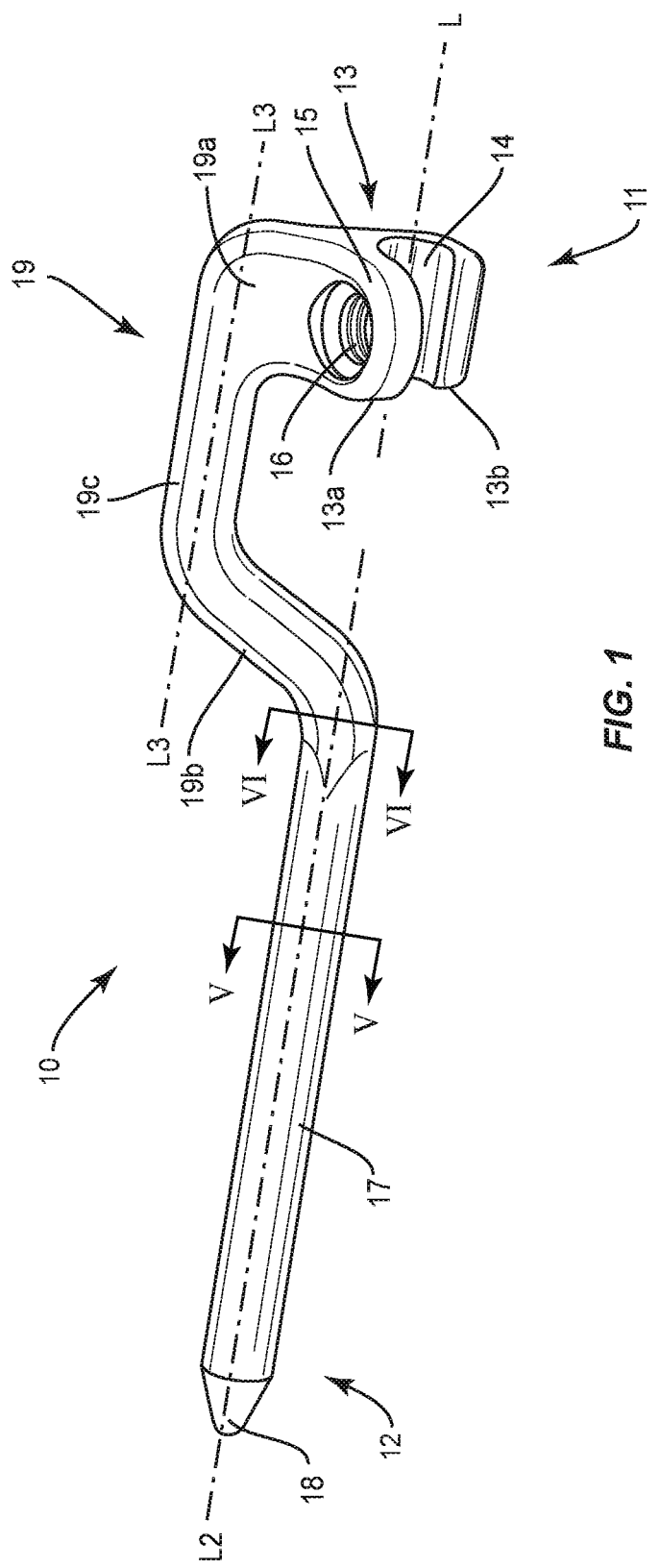
FIG. 1 is a perspective view of an embodiment of the percutaneous revision implant.

The exemplary embodiments of the invention and related methods of use disclosed are discussed in terms of medical devices for the treatment of musculoskeletal disorders and more particularly, in terms of a percutaneous revision implant and methods of using same to treat a spine.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present embodiments may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, upward, downward, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of the invention can be fabricated from biologically acceptable materials suitable for medical applications, including metals, synthetic polymers, ceramics and bone material and/or their composites, depending on the particular application and/or preference of a medical practitioner. For example, the components of the spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the spinal implant system may have material composites, including the above materials, to achieve various desired characteristics such as strength, rigidity, elasticity, compliance, biomechanical performance, durability and radiolucency or imaging preference. The components of the invention, individually or collectively, may also be fabricated from a heterogeneous material such as a combination of two or more of the above-described materials. The components of the invention may be monolithically formed, integrally connected or include fastening elements and/or instruments, as described herein.

For the purposes of promoting an understanding of the principles of the invention, reference will now be made to exemplary embodiments of the present disclosure, which are illustrated in the accompanying figures (FIGS. 1-10), and specific language will be used to describe the same. Alternate embodiments are also disclosed. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

In accordance with the present invention, a percutaneous revision implant is provided for percutaneously revising (e.g., extending) an existing implant located in the spine of a patient. More particularly, a percutaneous revision implant is provided that would accomplish revision of an existing implant in procedures that are minimally invasive, more particularly percutaneous, and will be useful for reducing or eliminating the need to significantly disrupt or remove an existing spinal implant or its components. The revision implant may comprise a single piece (i.e., monolithically formed). However, a revision implant with a minimal number of components, integrally connected or fastened with fastening elements and/or instruments, is also understood to be within the scope of the invention.

It is envisioned that the percutaneous revision implant of the invention will be employed, for example, with a minimally invasive procedure, including percutaneous techniques, mini-open and open surgical techniques, to deliver and introduce an implant, such as, for example, the percutaneous revision implant and new bone fastener disclosed herein, at a surgical site within a body of a patient, for example, a section of a spine. It is contemplated that the percutaneous revision implant and method may be employed with treatments using minimally invasive and percutaneous techniques.

Referring now to FIG. 1, shown therein is a percutaneous revision implant 10 according to one form of the present invention, for revising (e.g., extending) an existing implant located in a spine of a patient. Revision implant 10 includes a proximal end portion 11 and a distal end portion 12, and generally comprises a connector 13, a percutaneous rod 17, and an arm 19. In one embodiment, revision implant 10 may be monolithically formed.

Figure 2:
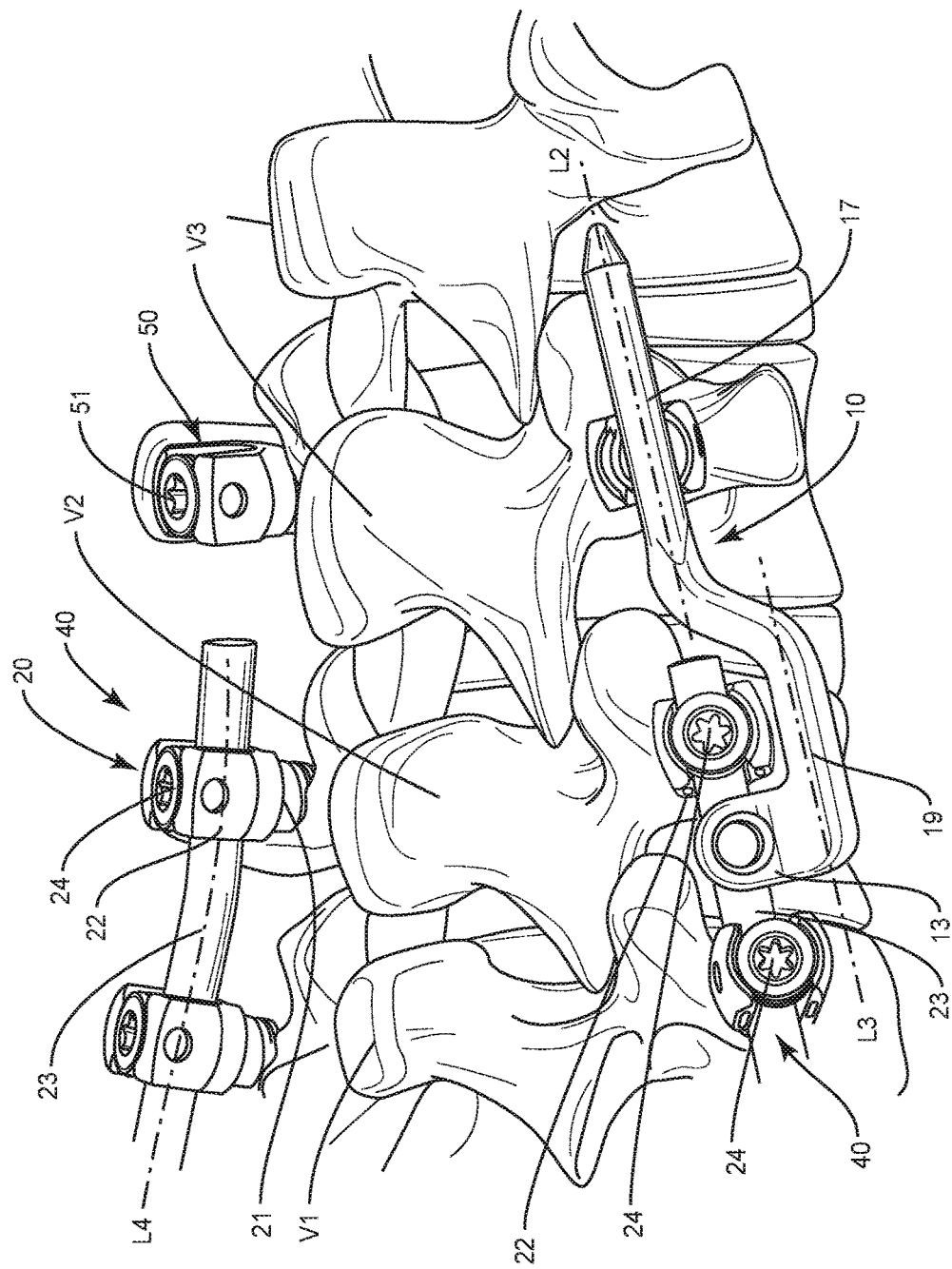
FIG. 2 is a perspective view of an embodiment of the spinal implant system attached to the spine.
Figure 7:
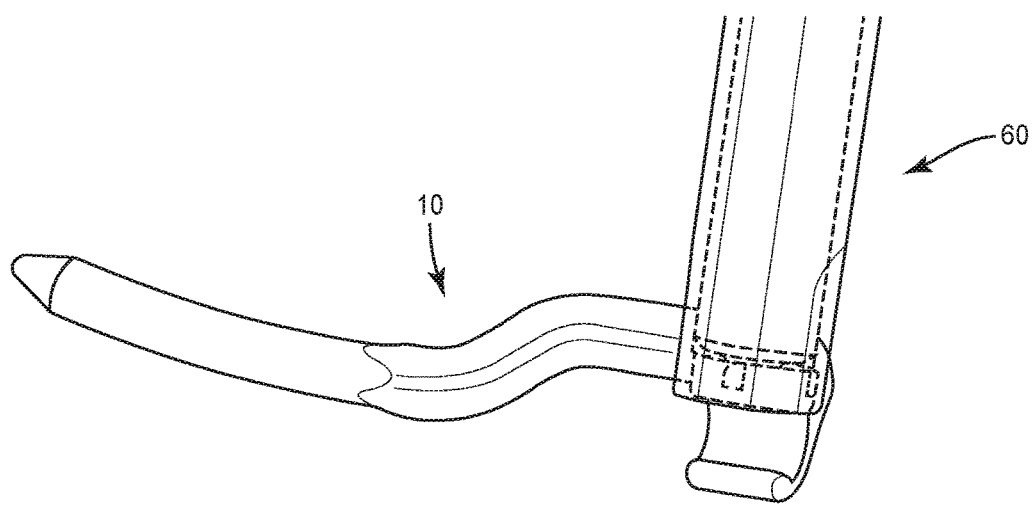
FIG. 7 is an enlarged perspective view of FIG. 1 engaged with a percutaneous delivery instrument.

Connector 13 comprises two opposable walls 13*a* and 13*b* joined at one end to define an inner cavity 14 having a longitudinal axis L. As illustrated in FIGS. 2 and 4, inner cavity 14 will be useful for accommodating a portion of an existing spinal implant component, such as existing spinal rod 23. Opposable walls 13*a* and 13*b* may comprise a clamp or pincer-like shape, and may be formed of rigid material. However, any configuration known in field to be suitable for engaging a rod is within the scope of the invention.

At least one of opposable arms 13*a* and 13*b* includes a threaded opening 16 extending from an outer surface 15 of the connector through to inner cavity 14. The threaded opening 16 will be useful for engaging a threaded set screw 51 in order to secure an engagement between connector 13 and a portion of a spinal implant, such as an existing spinal rod 23. Connector 13, and in particular threaded opening 16, may further be adapted for use with other kinds of fasteners known in the art (e.g., hooks, ties, wires).

In accordance with some embodiments of the invention, threaded opening 16 is configured to engage a threaded portion of a percutaneous delivery instrument, such as the aforementioned delivery instrument that is the subject of U.S. application Ser. No. 15/171,826, in order to facilitate percutaneous delivery and installation of the percutaneous revision implant to the intended surgical site in the spinal region of a patient by the user. In particular and as shown in FIG. 3, at least one of opposable arms 13a and 13b may comprise grooves or notches 30 for engaging and/or locking onto a percutaneous delivery instrument as in FIG. 7. The connector 13 may also comprise alternative features for engaging a delivery device, such as ribs, holes, or the like. In one embodiment, opposable arms 13a and 13b are adapted to be engaged by a component of a delivery device which may be manipulated by the user in order to lock and unlock the connection between percutaneous revision implant 10 and a delivery instrument.

In an alternative embodiment of the invention, connector 13 may be further adapted to allow for sagittal adjustment of connector 13 to permit the user to engage connector 13 with an existing spinal implant, such as existing spinal rod 23, at various angles relative to first longitudinal axis L of connector 13, in order to adjust the position of revision implant 10 as desired. For example, adapted connector 13 may facilitate the simultaneous active and passive correction or translation of fractured, degenerative or deformed vertebrae not only in the coronal plane but also in the dorsal-coronal, ventral-coronal, lateral-sagittal and medial-sagittal planes as well. Referring to FIGS. 8A-10, disposed within inner cavity 14 of connector 13 may be provided a seat 31 which may comprise any shape or configuration suitable to accommodate a sagittal adjuster 32. Seat 31 is typically a cavity (i.e. carve out) within inner cavity 14. Seat 31 may comprise a cross-like shape, but may also be oval, oblong, hemispherical, circular, elliptical, trianglular, rectangular, square, or polygonal, for example. Seat 31 may comprise a portion of walls 13a and/or 13b of the connector. In some embodiments, seat 31 will be provided with a surface configured to hold sagittal adjuster 32 within the seat and/or to facilitate the sliding movement of sagittal adjuster 32 with respect to existing rod 23 as described herein.

When seated in seat 31, sagittal adjuster 32 is adapted to slide within seat 31 along first longitudinal axis L and at angles to first longitudinal axis L. Sagital adjuster 32 may comprise various shapes and configurations. In some embodiments, sagittal adjuster 32 will comprise a shape having a polygonal cross-section (e.g., pentagonal). However, it will be understood that sagital adjuster 32 may be of any shape which will facilitate positioning of connector 13 on existing rod 13 at desired angles, and which not impede engagement of connector 13 with existing rod 23. Sagital adjuster 32 may also be provided with a concave configuration to facilitate engagement and fit with an existing implant, such as existing rod 23. A back surface 35 of connector 13 may be provided with a cavity 33 through which a portion of sagittal adjuster 32 may inserted to secure sagittal adjuster 32 in seat 31. In some embodiments, a hinge pin 34 may be used to ensure that sagittal adjuster 32 remains disposed within seat 31 during sliding movement.

Figure 8A:
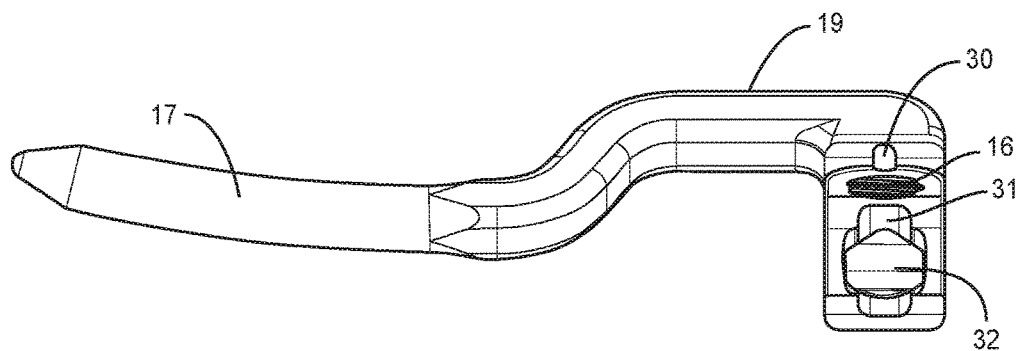
FIG. 8A is a front perspective view of an alternative embodiment of the percutaneous revision implant configured with sagitally adjustable connector.
Figure 8B:
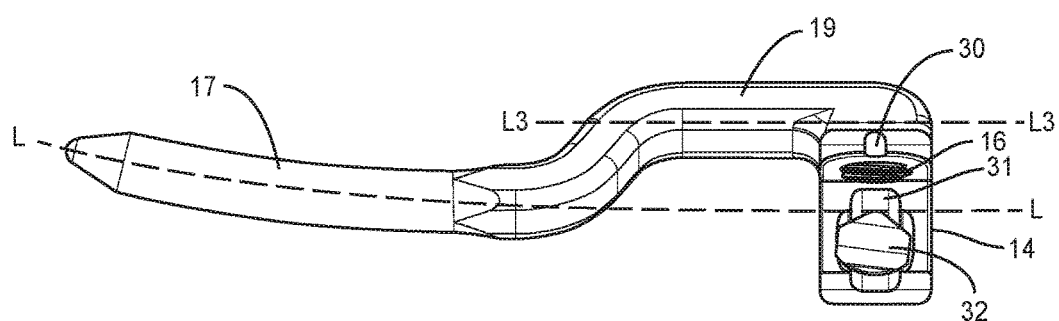
FIG. 8B is a front perspective view of FIG. 8A with an embodiment of the silo in a second position.
Figure 9:
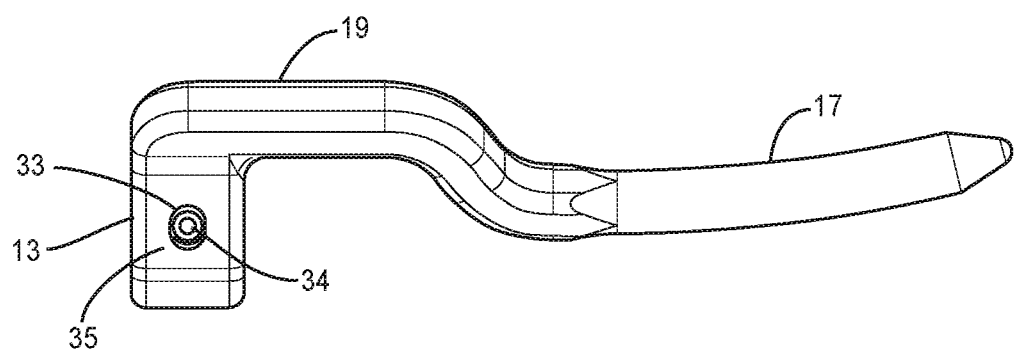
FIG. 9 is a back perspective view of FIGS. 8A and 8B.
Figure 10:
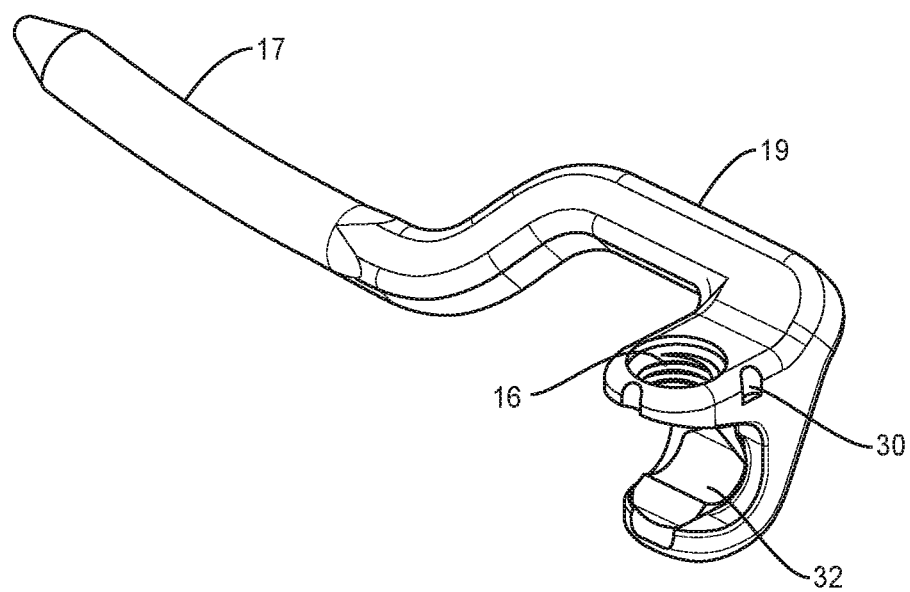
FIG. 10 is a side perspective view of FIGS. 8A and 8B.

Distal end portion 12 of revision implant 10 comprises a percutaneous rod 17 extending along a second longitudinal axis L2. In one embodiment, second longitudinal axis L2 is aligned or substantially aligned with first longitudinal axis L of connector 13. However, it will be understood that the revision implant 10 of the invention may comprise second longitudinal axis L2 of percutaneous rod 17 situated at an angle relative to first longitudinal axis L of connector 13, as shown in FIGS. 8A and 8B. Percutaneous rod 17 comprises a tip 18. In one embodiment, the percutaneous rod 17 is tapered such that a tip 18 of the rod comprises a diameter which is smaller than the diameter of any other portion of percutaneous rod 17. However, percutaneous rod 17 may be of any shape known in the field that permits physician medical practitioner to introduce or install the revision implant in the spine of a patient in a minimally invasive manner, preferably by gaining entry through a percutaneous puncture or stab in the skin of a patient. A portion of percutaneous rod 17 may comprise a cylindrical shape having a circular cross-section as in FIG. 5. In another embodiment, a portion of the percutaneous rod may comprise a polygonal shape having one or more beveled edges and a polygonal cross-section as in FIG. 6. However, percutaneous rod 17 may comprise other cross-section configurations that would facilitate introduction of revision implant 10 to a region of a spine through percutaneous surgical access site, including but not limited to, oval, oblong, trianglular, rectangular, square, polygonal, irregular, uniform, non-uniform, variable and/or tapered.

Percutaneous rod 17 may comprise a smooth or even outer surface defining a uniform thickness. It is envisioned, however, that rod 17 may have various surface configurations, such as, for example, rough, threaded for connection with surgical instruments, arcuate, undulating, porous, semiporous, dimple, polished and or textured according to the requirements of a particular application in a percutaneous-type revision procedure.

Revision implant 10 of the invention further comprises an arm 19 comprising a first transition region 19a joining arm 19 to connector 13, a second transition region 19b joining arm 19 to the percutaneous rod, and a linear portion 19c therebetween. Linear portion 19c defines a third longitudinal axis L3 which is offset from the first and second longitudinal axes L1 and L2. Arm 19 generally provides a means for stepping around and avoiding significant disruption or removal of the various components of existing implant 40, and in particular, bone fastener 20. The offset of third longitudinal axis L3 from longitudinal axes L and L2 allows a medical practitioner to position revision implant 10 at a surgical site in the spine adjacent an existing implant 40 (e.g., in a vertebral body adjacent another vertebral body having an existing implant installed therein) without removing or significantly disrupting (e.g., repositioning or removing) existing implant 40 or its components. For example, once revision implant 10 is installed, arm 19 provides a means to avoid disrupting at least one existing bone fastener 20 and/or rod 23 of existing implant 40. In one embodiment, arm 19 comprises a C-shape.

Proximal first transition region 19a joins connector 13 and linear arm portion 19c. First transition region 19a may be defined by a gradual transition from third longitudinal axis L3 to first longitudinal axis L. In one embodiment, first transition region 19a is sloped or angled upward A from connector 13.

Distal second transition region 19b joins percutaneous rod 17 and linear arm portion 19c. Second transition region 19b may be defined by a gradual transition from third longitudinal axis L3 of arm linear section 19c to second longitudinal axis L2 of percutaneous rod 17. In one embodiment, second transition region 19b may be sloped or angled upward A.

Percutaneous revision implant 10 may be of any length known in the art, provided that the length and orientation allow for installation by engaging an existing implant construct located in the spine of the patient (e.g., in a first vertebral body) and an adjacent portion of the spine (e.g., a second, adjacent vertebral body).

Revision implant 10 may further be formed of any suitable biocompatible material such as, for example, titanium, a titanium alloy, stainless steel, metallic alloys, or other materials known to those of skill in the art that possess the mechanical and biocompatible properties suitable for implantation within the body and attachment to bone.

As illustrated in FIG. 2, in a spinal surgical system according to the invention, the above-discussed percutaneous revision implant 10, an existing implant 40, and one or more new bone fasteners 50 are provided.

Existing implant 40 is understood to have been installed during one or more prior surgical procedures. Existing implant 40 generally comprises at least one or more existing bone fasteners 20 installed in one or more vertebra of the spine. Bone fasteners 20 comprise a shank 21 installed in the spine, and a receiver head 22 attached thereto. Existing implant 40 further comprises at least one existing rod 23, a portion of which is engaged by receiver head 22. In one embodiment, existing bone fasteners 20 are installed in a first vertebra V1 and a second vertebra V2. An existing rod 23 is engaged by receiver heads 22 of bone fasteners 20. Set screws 24 may also be included to secure existing rod 23 in place. Existing implant 40 may comprise additional components known in the field, including but not limited to, screws, plates, hooks, ties, and wires. While an embodiment of existing implant 40 spanning two vertebras is illustrated in FIG. 2, it is understood that existing implant 40 may span additional portions of the spine.

The spinal implant system of the present invention further comprises one or more new bone fasteners 50 for engaging percutaneous rod 17. In one embodiment, one or more new bone fasteners 50 are newly installed in at least one vertebra V3 adjacent the one or more vertebra V1, V2 having an existing implant installed therein as illustrated in FIG. 2. The one or more new bone fasteners 50, may be the same or similar to the above-described one or more bone fasteners 20 of existing implant 40, but may also be other bone fasteners known in the field suitable to engage a spinal rod, and in particular, percutaneous rod 17. The spinal implant system may further comprise a component for securing percutaneous rod 17 in bone fasteners 50, such as set screw 51. Other means for securing such engagement, including but not limited to screws, hooks, ties or wires, are within the scope of the invention.

In the spinal implant system, revision implant 10 may be oriented in various manners relative to existing implant 40, including in any manner that may be necessary to accommodate the unique dimensions of the various spinal structures of individual patients. In particular, revision implant 10 may be oriented to accommodate the natural curvature of the spine. In one embodiment, revision implant 10 is disposed to extend along an axial plane, such as for example, a sagittal plane of a body of a patient. Revision implant 10, however, may be disposed to extend along a coronal, sagital or transverse plane of the body and geometric variations thereof. In one embodiment, first and second longitudinal axes L1 and L2 align or substantially align with a longitudinal axis L4 of existing rod 23 once revision implant 10 is attached to the spine and engaged with the components of existing implant 40.

A method of using percutaneous revision implant 10 for percutaneously revising existing implant 40 to treat the spine of a patient is also provided. The method involves extending an existing spinal implant construct located in the spine of a patient, by employing aforementioned percutaneous revision implant 10, without removing or significantly disrupting existing implant 40 and/or its hardware components. Revision implant 10 may be used in any existing surgical method or technique including open surgery, mini-open surgery, minimally invasive surgery, and percutaneous surgical implantation.

The method of the present invention comprises the step of obtaining access to a post-operative spinal region of the patient having the existing implant installed therein and adjacent spinal regions as required for the particular application to provide one or more percutaneous access sites. In accordance with the present invention, one or more percutaneous access sites to a surgical site may be obtained in any appropriate manner, such as through incision and retraction of tissues in a minimally invasive manner or providing percutaneous stabs, punctures, micro-incisions, sleeves, protected passageways, or the like. The one or more incisions or punctures made in the body of the patient create one or a plurality of percutaneous surgical pathways and/or openings for implantation of components of the surgical system. For example, the surgical system is employed with a percutaneous surgical implantation such that a stab incision creates one or more percutaneous surgical pathways for delivering revision implant 10 and/or new bone fasteners 50 (e.g., pedical screw) to the surgical site. A preparation instrument (not shown) can be employed to prepare tissue surfaces of the vertebra (V1, V2, V3, etc.), as well as for aspiration and irrigation of a surgical region according to the requirements of a particular surgical application.

Once percutaneous surgical pathway is obtained, the particular surgical procedure is performed for treating the spinal disorder, and for extending or other revising the existing implant. The components of the spinal system are then employed to augment the surgical treatment. One or all of the components of the surgical system may be completely or partially revised, removed or replaced during or after the surgical procedure.

The method further comprises the steps of installing one or more new bone fasteners 50 in a portion of the spine adjacent the spinal region having existing implant 40 implanted therein through the one or more percutaneous access sites or surgical pathways. One or more new bone fasteners 50 may be installed in at least one vertebra adjacent the one or more vertebra V1, V2 having an existing implant installed therein, such as adjacent vertebra V3 illustrated in FIG. 2. In one embodiment, the method further comprises installing bone fastener 50 by accessing the adjacent vertebra V3 through the same percutaneous puncture used to introduce revision implant 10 to the surgical site. Bone fastener 50 may be installed at any point during the procedure which allows for the desired placement of percutaneous revision implant 10 to treat the spine of the patient.

The method further comprises the step of introducing revision implant 10 through a percutaneous access site and surgical pathway, engaging existing rod 23 with connector 13, and engaging percutaneous rod 17 with one or more new bone fasteners 50. In one embodiment, the method further comprises securing the engagements of existing rod 23 with connector 13 and/or the coupling of percutaneous rod 17 with bone fastener 50, such as with set screws 24 and 51 or other securing means (e.g., ties, wires, hooks) known in the art. In some embodiments, the method is performed entirely through one percutaneous access site and surgical pathway.

The method may employ a percutaneous delivery instrument for percutaneously delivering and installing percutaneous revision implant 10, set screw 51, and/or other components to a surgical site in the spinal region of a patient, for example the percutaneous delivery instrument disclosed in pending U.S. patent application Ser. No. 15/171,826. The disclosures of U.S. patent application Ser. No. 15/171,826, including the method of using the present percutaneous revision implant 10 with the delivery instrument disclosed therein to revise an existing implant located in the spine of a patient, are incorporated herein. In particular, according to the disclosures therein, by engaging or locking notches, grooves, ribs or like features of the delivery instrument with the aforementioned notches or grooves 30 located on one or more of opposable walls 13a and 13b of the present invention, the medical practitioner may introduce, install, and position revision implant 10 and other surgical components in a precise manner during a percutaneous-type revision procedure.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

The invention claimed is:

1. A percutaneous revision implant for percutaneously revising an existing implant located in a spine of a patient, said revision implant comprising:
   a proximal end portion comprising a connector for engaging an existing rod, said connector comprising two opposable walls joined at one end to define a cavity having a first longitudinal axis, at least one of said opposable walls comprising a threaded opening;
   a distal end portion comprising a percutaneous rod integrally formed with said connector, said rod extending along a second longitudinal axis; and
   an arm comprising a first transition region connecting said connector to the arm, a second transition region connecting the percutaneous rod to the arm, and a linear portion, said linear portion having a third longitudinal axis, the third longitudinal axis extending parallel to the first and second longitudinal axes, the linear portion being positioned between the first transition region and the second transition region,
   wherein a top surface of the first transition region slopes toward the linear portion in an upward direction from a top surface of one of the opposable walls, and
   wherein the top surface of the one of the walls and a top surface of the linear portion are coplanar.

2. The revision implant of claim 1, at least one of said opposable walls further comprises grooves to engage a percutaneous delivery instrument.

3. The revision implant of claim 1, wherein the connector is formed of a rigid material.

4. The revision implant of claim 1, wherein the threaded opening is adapted for engaging a threaded set screw.

5. The revision implant of claim 1, wherein the threaded opening is adapted for engaging a threaded portion of a percutaneous delivery instrument.

6. The revision implant of claim 1, wherein said connector comprises one or more grooves in at least one of the walls of the connector.

7. The revision implant of claim 1, wherein a tip of the percutaneous rod is tapered.

8. The revision implant of claim 1, wherein the percutaneous rod comprises a polygonal cross-section.

9. The revision implant of claim 1, wherein the arm is C-shaped.

10. The revision implant of claim 1, wherein at least one of the first and second transition regions is sloped or angled.

11. The revision implant of claim 1, wherein the second longitudinal axis is coaxial with the first longitudinal axis.

12. The revision implant of claim 1, wherein the walls are joined at the one end by a back surface, the back surface including a cavity having a hinge pin therein, the walls defining a seat that is in communication with the cavity, the seat having an adjuster slidably positioned therein, the adjuster engaging the hinge pin to ensure that the adjuster remains within the seat during sliding movement.

13. The revision implant of claim 1, wherein the second transition region slopes downwardly from the linear portion to the percutaneous rod.

14. The revision implant of claim 1, wherein the second transition region slopes toward the percutaneous rod in a downward direction from the top surface of the linear portion.

15. The revision implant of claim 1, wherein the percutaneous rod is formed with the connector into a single piece.

16. The revision implant of claim 1, wherein the second transition region extends transverse to the axes.

17. A spinal implant system for percutaneously revising an existing implant located in a spine of a patient comprising at least one existing bone fastener comprising a shank and a receiver head attached thereto, and further comprising at least one existing rod engaged in the receiver, the spinal implant system comprising:
   a percutaneous revision implant comprising a proximal end portion comprising a connector for engaging an existing rod, said connector comprising two opposable walls joined at one end to define a cavity having a first longitudinal axis, at least one of said opposable walls comprising a threaded opening;
   a distal end portion comprising a percutaneous rod integrally formed with said connector, said percutaneous rod extending along a second longitudinal axis; and
   an arm comprising a first transition region connecting said connector to the arm, a second transition region connecting the percutaneous rod to the arm, and a linear portion, said linear portion having a third longitudinal axis extending parallel to the first and second longitudinal axes, the first transition region extending transverse to the axes; and
   one or more new bone fasteners for screwing into a portion of the spine adjacent to a portion of the spine of the patient having the existing implant installed therein,
   wherein a top surface of the first transition region slopes toward the linear portion in an upward direction from a top surface of one of the opposable walls, and
   wherein the top surface of the one of the walls and a top surface of the linear portion are coplanar.

18. The spinal implant system of claim 17, wherein at least one of the opposable walls comprises grooves to engage a percutaneous delivery instrument.

19. A spinal implant comprising:
   a connector comprising spaced apart walls that define a cavity therebetween, the cavity defining a first longitudinal axis, one of the walls comprising a threaded opening;
   a rod integrally formed with the connector, the rod extending along a second longitudinal axis; and an arm joining the connector with the rod, the arm comprising a first transition region extending from the connector, a second transition region extending from the rod and a linear portion between the transition regions, the linear portion defining a third longitudinal axis that extends parallel to the first and second longitudinal axes, wherein a top surface of the first transition region slopes toward the linear portion in an upward direction from a top surface of one of the walls, and wherein the top surface of the one of the walls and a top surface of the linear portion are coplanar.

20. The spinal implant of claim 19, wherein the walls are joined by a back surface, the back surface including a cavity having a pin therein, the cavity having an adjuster slidably positioned therein, the adjuster engaging the pin to ensure that the adjuster remains within the cavity during sliding movement.

\* \* \* \* \*